United States Patent [19]

McGrail et al.

[11] Patent Number: 5,974,859
[45] Date of Patent: Nov. 2, 1999

[54] METHOD AND APPARATUS FOR MEASURING COUPLED FLOW, TRANSPORT, AND REACTION PROCESSES UNDER LIQUID UNSATURATED FLOW CONDITIONS

[75] Inventors: Bernard P. McGrail, Pasco; Paul F. Martin; Clark W. Lindenmeier, both of Richland, all of Wash.

[73] Assignee: Battelle Memorial Institute, Richland, Wash.

[21] Appl. No.: 09/020,697

[22] Filed: Feb. 9, 1998

[51] Int. Cl.[6] ............................ G01N 15/08; E21B 49/00
[52] U.S. Cl. ............................................. 73/38; 73/152.05
[58] Field of Search ................................... 73/38, 152.05

[56] References Cited

U.S. PATENT DOCUMENTS

| | | |
|---|---|---|
| 4,253,327 | 3/1981 | Wiley ............................................. 73/38 |
| 4,506,542 | 3/1985 | Rose .............................................. 73/38 |
| 4,672,840 | 6/1987 | Cullick ......................................... 73/38 |
| 4,773,254 | 9/1988 | Shen ............................................. 73/38 |
| 5,299,140 | 3/1994 | Ankeny et al. .............................. 73/38 |
| 5,731,511 | 3/1998 | Roque et al. ................................ 73/38 |
| 5,858,791 | 1/1999 | Lemaire ...................................... 73/38 |

*Primary Examiner*—William Oen
*Assistant Examiner*—Robin C. Clark
*Attorney, Agent, or Firm*—Paul W. Zimmerman

[57] ABSTRACT

The present invention is a method and apparatus for measuring coupled flow, transport and reaction processes under liquid unsaturated flow conditions. The method and apparatus of the present invention permit distinguishing individual precipitation events and their effect on dissolution behavior isolated to the specific event. The present invention is especially useful for dynamically measuring hydraulic parameters when a chemical reaction occurs between a particulate material and either liquid or gas (e.g. air) or both, causing precipitation that changes the pore structure of the test material.

13 Claims, 6 Drawing Sheets

5,974,859

METHOD AND APPARATUS FOR MEASURING COUPLED FLOW, TRANSPORT, AND REACTION PROCESSES UNDER LIQUID UNSATURATED FLOW CONDITIONS

This invention was made with Government support under Contract DE-AC0676RL01830 awarded by the U.S. Department of Energy. The Government has certain rights in the invention.

FIELD OF THE INVENTION

The present invention relates generally to a method and apparatus for measuring coupled flow, transport and reaction processes under liquid unsaturated flow conditions in a porous material.

Liquid includes but is not limited to organic liquid, for example hydrocarbons including gasoline, oil, PCB (polycarbonatebiphenyl) and combinations thereof, inorganic liquid including but not limited to water, silanes and combinations thereof.

Porous material is any material with a structure defining a plurality of tortuous paths through the porous material through which a liquid may flow in an unsaturated state, including but not limited to soil, crushed glass or rock, other particulate, sponge, paper, membrane or filter material, charcoal, activated carbon and combinations thereof.

Unsaturated is a two phase condition within the volume of the pores of a porous material wherein less than 100% of the pore volume is filled with liquid. When the pore volume is filled 100% with a liquid, the porous material is liquid saturated or, simply stated, saturated. The second phase is a gas, typically air that is contained in the remaining pore volume that is not filled with the liquid. In the case of the pore volume being 100% filled with a gas and no liquid is present, that is a single phase condition referred to as a dry condition that is not unsaturated.

Reaction process includes chemical reaction and physical reaction that can alter pore structure or pore volume. When a chemical reaction occurs between a particulate material and either liquid or gas (e.g. air) or both, a reaction product including but not limited to precipitation, erosion, oxidation, and combinations thereof can occur that can change the pore structure of the porous material. This can affect liquid flow through the porous material; both reduction or increase in flow rate are possible. A physical reaction includes but is not limited to sedimentation, i.e. introduction of smaller particulate that can reduce pore volume, cracking that may be induced by freeze/thaw cycles thereby either increasing or decreasing porosity (pore volume), erosion, compaction, vibration, radiation, heat, and combinations thereof.

BACKGROUND OF THE INVENTION

Groundwater quality is increasing in importance and assessing it requires understanding flow and transport processes under unsaturated conditions. Because the physics of unsaturated flow is a highly non-linear function of porosity, permeability, and water retention characteristics (Zhang and van Genuchten 1994), relatively small changes in these properties, induced from chemical reactions, can significantly alter the hydraulic characteristics of a porous medium. Despite this acknowledged significance of reaction-induced changes in hydraulic properties of porous and fractured media (e.g. rocks), little experimental work has been done to quantify the processes involved; most of the work has relied on modeling simulations only. For example, Ortoleva et al. (1987) and Chen et al. (1990) have simulated coupled flow and reaction processes related to advanced oil recovery. Hoefner and Fogler (1988), Sanford and Konikow (1989), Steefel and Lasagna (1990), and Steefel and Lichtner (1994) have simulated porosity/permeability and transport property changes in response to dissolution/precipitation reactions. Smoot and Sagar (1990) inferred from model simulations that the hydraulic conductivity of the soil underneath a waste storage tank at Hanford was halved by leaking hyperalkane liquid.

Using a constant head permeameter, Goldenberg, Margaritz, and Mandel (1983), and Raffensperger and Ferrel (1991) showed how the permeability of sand/clay mixtures changes in response to the infiltration of NaCl and $CaCl_2$ solutions under saturated conditions.

Columns and/or flow cells filled with particulate, eg soil, have been known and used for years for measuring particulate parameters, for example hydraulic conductivity and diffusivity both for saturated and unsaturated particulate/soil. The book *METHODS OF SOIL ANALYSIS*, Arnold Klute, Editor, 1986, section 28–5 shows a flow cell system for steady-state measurement of hydraulic conductivity of unsaturated soils (FIG. 1). The soil 100 is held in a column 102 between an upper plate 104 and a lower plate 106. In operation, the system is used for steady-state determination of hydraulic conductivity with a time-invariant one-dimensional flow of the liquid phase at a given water content. Disadvantages of this system include (1) only a time averaged value of conductivity is obtained, (2) only soil with porosity less than a "bubble pressure plate porosity" can be tested, and (3) only pressure and/or temperature conditions that are within the operating limit of the bubble pressure plate are useable/testable. In other words, instantaneous value of conductivity is not possible, nor are measurements requiring gas pressure greater than the bubble pressure of the upper plate 104 possible using this prior art system.

Another common column is the Wierenga column (FIG. 2) useful for measuring hydraulic conductivity of a particulate (soil) sample under unsaturated conditions. Similar in construction with the flow cell, a column body 200 has a base 202 bubble pressure plate 204 with an effluent drain port 206 through the base 202. A tensiometer port 208 with a tensiometer bubble pressure plate 210 and tensiometer access tube 212 is used to measure water tension. The upper portion of the column is the mirror image of the base including a bubble pressure plate and a tensiometer port. Fluid is introduced into the column through a influent port which is identical in construction to the drain port. Flow through a Wierenga column is achieved by creating a hydraulic head pressure and using gravity as the driving force. Unsaturated conditions within the column are achieved by resticting flow and drawing a low pressure or vacuum on the effluent drain port 206. The upper limit of pressure (as vacuum) that may be imposed upon the Wierenga column is determined by the rating of the bubble pressure plates and the column's construction. As designed, these columns typically have an operational limit of −0.137 bar. Again, the Wierenga column has similar disadvantages as the flow cell described above. Both the flow cell and Wierenga columns are designed for steady-state measurements of hydraulic conductivity or water retention characteristics of soils at room temperature. It is assumed in these tests that water percolating through the apparatus is not altering the test material either physically or chemically.

Prior art columns designed for hydraulic property measurements are intended to provide a single data point at a specific hydraulic steady state that is achieved as rapidly as possible. Reactions, including chemical reactions between the fluid and the porous material, are not monitored nor considered. Water is passed through the column containing a porous material in a single step and weighing the effluent or weighing the filled column or both is all that has been required to obtain the hydraulic data of interest. Because the onset of a dissolution or precipitation reaction is unpredictable, taking days or months of exposure to a fluid under reacting conditions, and because once a change in porosity even begins, the change can come to completion quickly, it would not be possible to observe the change in porosity event and any transient effect upon flow with prior art columns. Any change of hydraulic condition of the porous material during operation of a prior art column would simply be averaged in the final result.

Hence, there remains a need in the art of measuring hydraulic characteristics of soils or other test material for an apparatus and method for dynamically measuring hydraulic characteristics wherein a reaction (physical or chemical) alters the hydraulic characteristics of the porous material.

SUMMARY OF THE INVENTION

The present invention is a method and apparatus for measuring coupled flow, transport and reaction processes under liquid unsaturated flow conditions in a porous material. The method and apparatus of the present invention permit distinguishing individual precipitation events and their effect on dissolution behavior isolated to the specific event.

The present invention permits collection of data at a sufficiently small time interval so that individual precipitation events may be separated and their effects on flow (if any) identified. The method has the steps of:

(a) placing a porous material in a vessel, the vessel having porous plate below the porous material, the particulate sample having an amount of a liquid and an amount of a gas in an unsaturated condition;

(b) maintaining the unsaturated condition by regulating liquid and gas flow rate, pressure, and temperature (c) monitoring in real time volumetric water content in the column, and effluent chemical properties including pH and electrical conductivity; and (d) collecting effluent from an outlet for subsequent chemical analysis.

Additional parameters measured include a porous material bulk temperature, a vessel pressure, the liquid flow, the gas flow, the effluent chemistry, and combinations thereof as a function of time and at intervals of a maximum of 1 hour during the maintaining.

The apparatus has (a) a vessel having a porous plate at a bottom end placed below a porous material, the porous material having an amount of a liquid and an amount of a gas in an unsaturated condition;

(b) a liquid inlet flow port at the top and an outlet for collecting effluent; and (c) instruments for measuring parameters of a porous material bulk temperature, a vessel pressure, the liquid flow, and effluent chemistry, and combinations thereof, during the maintaining.

Accordingly, the present invention represents the first time that the coupling between secondary phase precipitation, and unsaturated flow hydraulics in a porous material has been quantitatively measured. This method was the first demonstration that unsaturated flow-through conditions establish significant differences in solution pH and elemental release behavior of a waste glass as compared with water-saturated tests. Thus, the present invention has an advantage of more accurate evaluation of long term behavior in unsaturated systems compared to the use of water-saturated batch tests, like the Product Consistency Test. Another advantage of the present invention is that experiments with a low-activity waste glass also showed that the onset of secondary phase precipitation was achieved as much as 20 times faster compared with standard, batch saturated methods (e.g. PCT) at the same temperature. Thus, the method of the present invention provides a new means of accelerating glass/water reactions without going to high temperatures.

It is an object of the present invention to provide a method and apparatus for measuring coupled flow, transport, and reaction processes in liquid unsaturated flow conditions within a porous material wherein parameters are measured at a time interval of 1 hour or less.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 3:
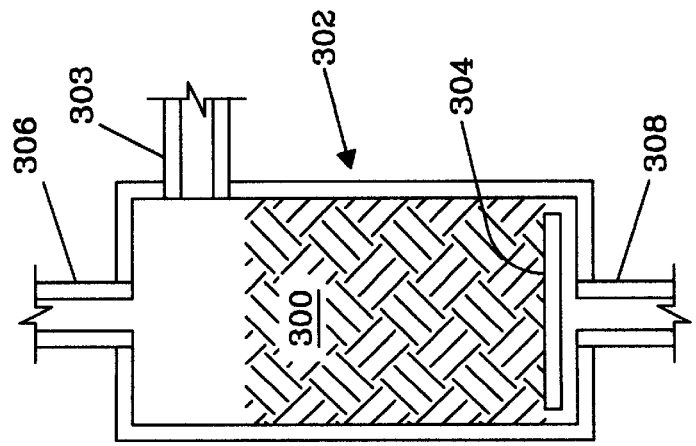
FIG. 3 is a cross section of a column according to the present inventions.
Figure 2:
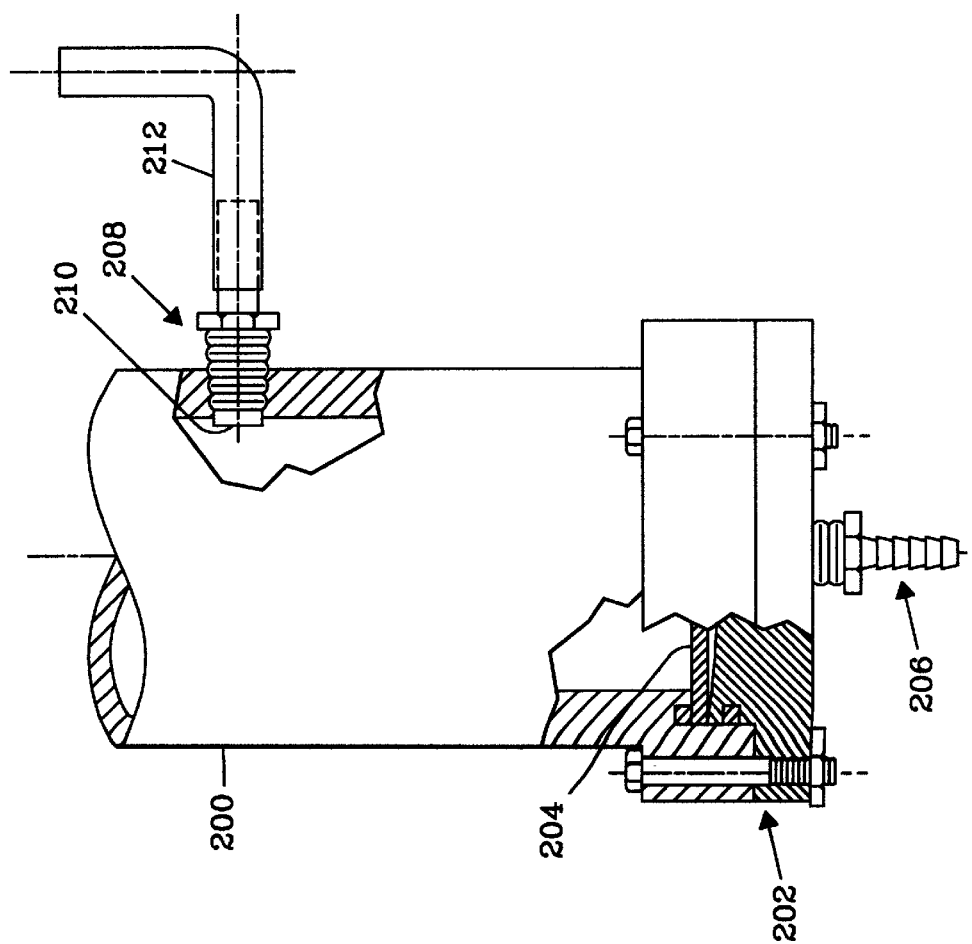
FIG. 2 is a cut-away of a prior art Wierenga column.

In order to maintain an unsaturated condition in a porous material 300, the column 302 containing the porous material 300 must be designed (FIG. 3) to 1) vary the volumetric water content from at least 20% of saturation to 100% of saturation, 2) minimize the flow rate to decrease saturation level, and 3) operate at a maximum temperature of 90° C. Unsaturated conditions are established by applying gas pressure through a pressure port 303 across a semi-permeable, porous plate 304. The pressure port 303 is located at or near the top of the column 302. Gas is both replenished and vented through the pressure port 303. Liquid is introduced through a liquid port 306. When water-saturated, the porous plate 304 allows water but not air to flow through it, as long as the applied pressure differential does not exceed the air entry relief pressure or bubble pressure of the plate. Titanium was chosen for the porous plate 304 because it is highly corrosion resistant and has excellent wetting properties. The column 302 is fabricated from a chemically inert material, for example polyetheretherketone (PEEK), so that dissolution reactions are not influenced by interaction with the column 302, nor is the effluent passing through the effluent port 308 contaminated by contact with the column 302.

The column 302 may be mounted on a vibrator, moved from oven to freezer to simulate freeze/thaw, mounted on a controllable heat transfer unit (heater, cooler, or combination thereof) to achieve physical reactions. In addition, the column 302 may have a sediment port (not shown) permitting introduction of additional particulate.

Figure 4A:
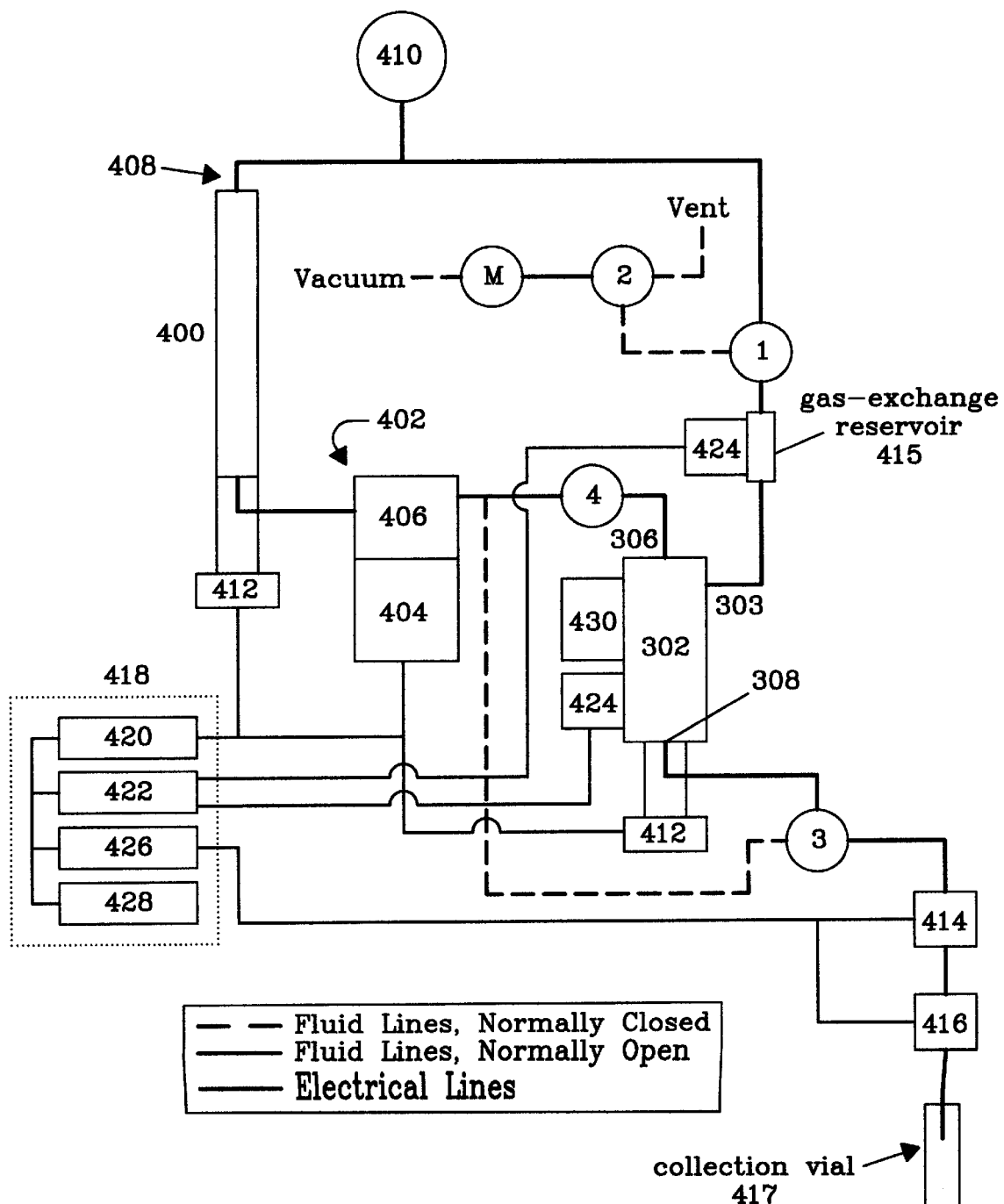
FIG. 4a is a schematic of a system according to the present invention incorporating the column of FIG. 3.
Figure 4B:
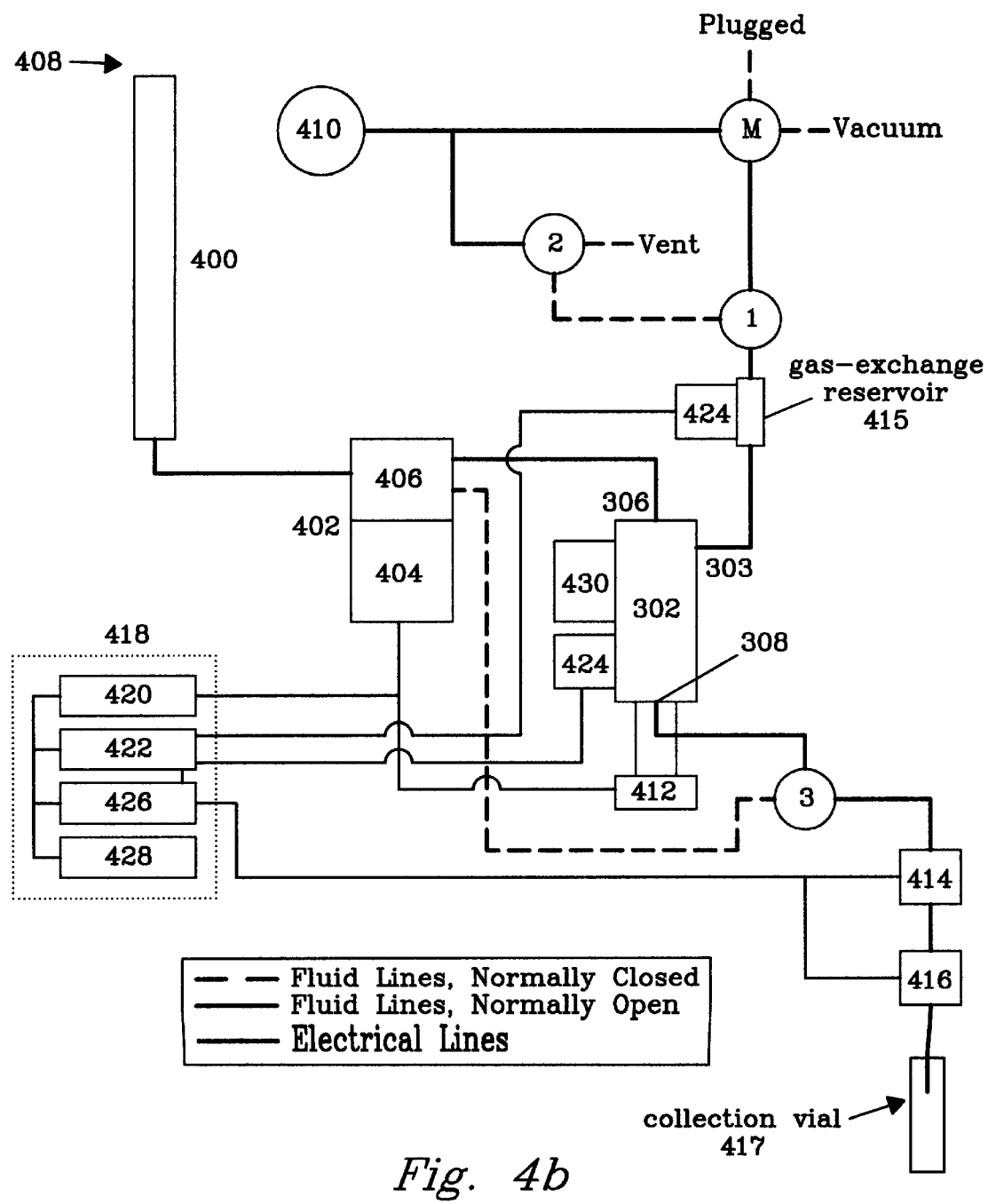
FIG. 4b is an alternative schematic of the system of the present invention incorporating the column of FIG. 3.

Operation of the column 302 is computer controlled to enable rapid data collection. The overall system is shown in FIG. 4a. The column 302 receives liquid from an influent reservoir 400, with the liquid passing through a pump and valve assembly 402 having a pump 404 and valve(s) 406 that are used to direct liquid to or from the column 302 through the influent port 304. The influent reservoir 400 receives liquid through a fill port 408. Gas pressure is supplied through a gas regulator 410. The influent reservoir 400 and the column 302 are each set on a balance 412 for dynamic or real time mass tracking. Optionally (FIG. 4b), only the column 302 is set on a balance 412. Effluent from the column 302 passes through a conductivity cell 414, then to a pH probe 416.

Two solenoid valves 1, 2 and a manual valve M are attached to the pressure port 303 to permit periodic venting and repressurization of the column. These valves enable automatic gas exchange to occur on a frequent basis to minimize the depletion of any reactive gases in the column 302. The valves are configured so that, after repressurization, the column 302 may be operated normally open to pressure or normally closed to pressure. A gas-exchange reservoir 415 is attached to the pressure port 303 to collect any small amount of liquid that is lost during venting. The liquid collected in the gas-exchange reservoir is then reintroduced to the column 302 when it is repressurized. Liquid effluent passes through a third solenoid valve 3 to a collection vial 417. Solenoid valve 4 is a shut-off valve.

A dedicated computer 418 running LabVIEW™ software controls test parameters and logs test data to a disk. Within the computer 418, instrument communication 420 controls and collects data from the pump 404 and the balances 412. Signal conditioning and data acquisition 422 within the computer 418 controls and receives data from several sensors 424 including but not limited to thermocouples, pressure sensors, gas (e.g. $CO_2$) sensors, motion sensors, and combinations thereof, and receives data from conductivity and pH probe electronics 426 connected to the conductivity probe 414 and the pH probe 416. A standard user interface 428 includes keyboard and display screen. The computer 418 simultaneously controls both column temperature and pump for influent delivery capable of flow rates ranging from 0.01 to 100 mL/h.

An environmental unit 430 may be a heater, cooler, vibrator, compactor, or combination thereof for varying reaction conditions within the column 302.

Operational modes are shown in Table 1 as defined by valve position and pump status. The operator selects a mode and activates the regular (periodic) cycle beginning at that mode. The mode will operate until it is toggled off. Alternatively an automatic control with a feedback loop connected to a sensor (e.g. temperature or CO2-sensor) may be used.

TABLE 1

| | Operational Modes | | | | | | |
|---|---|---|---|---|---|---|---|
| Valv Mode/ | 1 | | 2 | | 3 | | |
| Valve Port[1] | NO | NC | NO | NC | NO | NC | Manual[2] | Pump |
| Saturate | ● | | ● | | | ● | Vacuum | On |
| Desaturate | ● | | ● | | ● | | Pressure | Off |
| Normal (NOTP[3]) | ● | | ● | | ● | | Pressure | On |
| (Vent-NOTP) | | ● | | ● | ● | | Pressure | Suspend |
| Normal (NCTP[4]) | ● | | ● | | ● | | Closed | On |
| (Vent-NCTP) | | ● | | ● | ● | | Closed | Suspend |
| (Pressurize-NCTP) | ● | | ● | | ● | | Closed | On |

[1]3-way solenoid valve. NO: Normally Open to common port, NC: Normally Closed.
[2]"L" flow pattern (two adjacent ports open to each other) 4-port valve used as 3-way valve.
[3]NOTP: Normally Open to Pressure, manual valve set to pressure connection. Automatic venting (hourly or daily) is a two step process: Vent then return to normal.
[4]NCTP: Normally Closed to Pressure, manual valve set to plugged position. Automatic venting (hourly or daily) is a three step process: Vent, pressurize then return to normal.

When the operator selects one of the periodic venting modes (Hourly Vent or Daily Vent) the software triggers the solenoid valves 1, 2 at regular intervals. When the column 302 is operating in Normally Open to Pressure (NOTP) mode the valves first vent the column then return to normal. When the column is operating in Normally Closed to Pressure(NCTP) mode the column is first vented then pressurized then re-turned to normal. Switching between NOTP and NCTP is accomplished by moving the manual valve M to the appropriate position.

EXAMPLE 1

An experiment was conducted to model or simulate disposal of high-level radioactive waste in a deep geologic repository, located at the Yucca Mountain site in the state of Nevada. Because this repository is located above the present water table in the unsaturated zone, understanding the corrosion behavior of this waste glass under unsaturated conditions is of fundamental importance.

In this experiment, a nonradioactive, reference high-level waste glass, composition identified as SRL-202 (Ebert and Bates 1993) was used. The glass was prepared by crushing and screening to obtain the −20+70 mesh (210 to 841 $\mu$m) size fraction, then by cleaning according to standard methods (ASTM 1994). The column 302 was filled with the prepared glass, giving an initial porosity of approximately 0.4, and was then vacuum saturated with water at ambient temperature.

A temperature controller was programmed to heat the column to 90° C. in about 2.5 hour (0.6° C./minute). The column was initially desaturated by injecting air with a gas-tight syringe through the pressure port 303 and the displaced effluent was collected. The influent pump was valved off and the column 302 was vented periodically through the pressure port 303 during the temperature ramp to maintain an internal pressure less than the bubble pressure of the porous plate 304.

After reaching 90° C., the influent valve 406 was opened and influent and effluent flow rates were set equal at 2.0 ml per day. The column was pressurized with air supplied by a regulated pressure source. Effluent samples were collected in a receiving vessel, which was periodically drained into tared vials from which samples were extracted for elemental analysis by ICP-AES.

After test termination, the reacted glass material was then carefully scraped out to a series of controlled depths and transferred to tared vials. The filled vials were weighed and then moved to a vacuum oven operating at 35–40° C. and dried until a constant weight was obtained. The amount of glass recovered was compared to the amount initially packed into the column. The final volumetric water content in the column was also calculated from these final weights. Samples from the bottom, middle, and top of the column were analyzed for major crystalline phases by powder XRD, SEM, and TEM.

Figure 5:
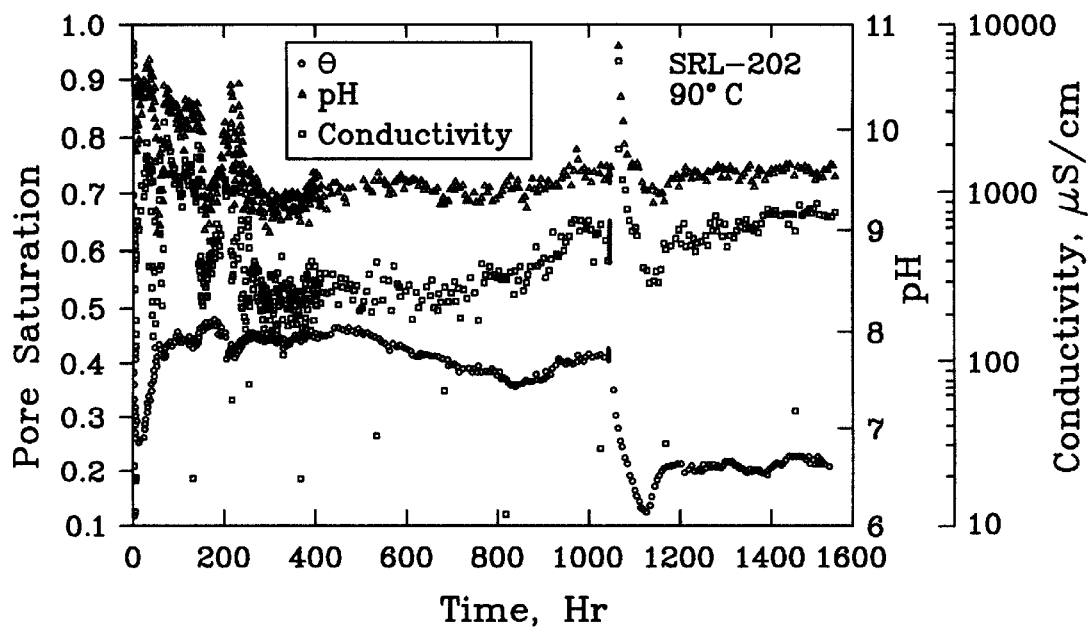
FIG. 5 is a graph of pore saturation, conductivity and pH versus time.

FIG. 5 shows the time-dependent variation in the pore saturation and effluent pH. The computer data logging system provides a high data density so that changes in effluent chemistry and water content can be clearly correlated. The spikes in effluent pH observed at various times during the test are indicative of precipitation of secondary phases.

Precipitation of secondary phases can directly change the pH through the consumption/release of H+, or indirectly by increasing or decreasing the dissolution rate of the glass. Dissolution rates of silicate glasses are sensitive to variations in solution chemistry, particularly to concentrations of orthosilicic acid ($H_4SiO_4$). Precipitation of secondary phases that contain Si can lower the concentration of $H_4SiO_4$ and so increase the glass reaction rate.

The effects of the dissolution/precipitation events on hydraulic properties can be clearly observed. For example, multiple precipitation events are observable in the pH trace up to about 200 hours into the test. These events clearly caused changes in the hydraulic properties of the porous glass bed. Later in the test, a pseudo steady-state appeared to have been reached with pore saturation remaining between 40 to 45% until about 1050 hours, when a precipitation event occurred that caused a spike in the effluent pH. After this event, the column drained over a period of several days, which reduced the amount of water by more than half.

Figure 6:
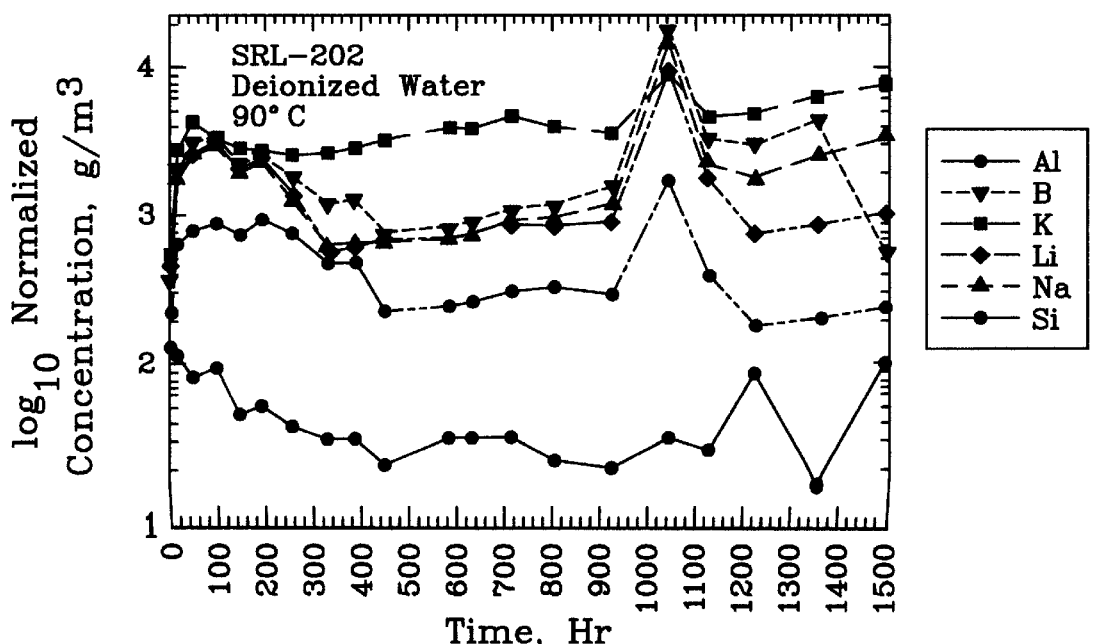
FIG. 6 is a graph of log normalized concentration versus time.

FIG. 6 shows the time-dependent normalized concentrations of the major glass components in the effluent samples. The time-dependent variation in the solution concentrations of the major glass components correlates with the variation in moisture content over this same time period (FIG. 5). Initial release of B and the alkali metals (Li, Na, K) is congruent. After a precipitation event at approximately 210 hours into the test, differentiation in the elemental release rates is observed. At the last data point available, the elemental release rates follow the sequence K>;B>;Li=Na=Si>;Al and solution pH was approximately 9.3. The sequence in the 20,000 $m^{-1}$ PCT results reported by Ebert and Bates (1993), before a rate acceleration was observed, is B>;Li>;Na=K>;Si and solution pH was 11.0 to 11.4. Unsaturated flow-through conditions establish a fundamentally different physical and chemical environment from the glass/water reaction as compared with water-saturated batch tests. The corrosion rate acceleration observed at 1100 h, indicated by the unexpected jump in solution concentrations, may correspond to the rate acceleration observed in the PCTs after 182 days. Unlike the static PCT results, however, the rate acceleration was clearly transient under unsaturated flow-through conditions. In a closed-system test, like the PCT, the effects of secondary precipitation on the solution composition are cumulative, and thus can have a cascading effect on glass dissolution behavior.

EXAMPLE 2

Another experiment was conducted using a doped ceramic simulated waste form having a primary phase of zirconolite ($CaM_xZr_{1-x}Ti_2O_7$), where the dopant M is a tetravalent metal ion, Ce4+ in this experiment. The ceramic also has minor amounts of the phases Ba-hollandite and pyrochlore. The Ce-doped ceramic simulated waste form was exposed to a temperature of 90° C.

Figure 7:
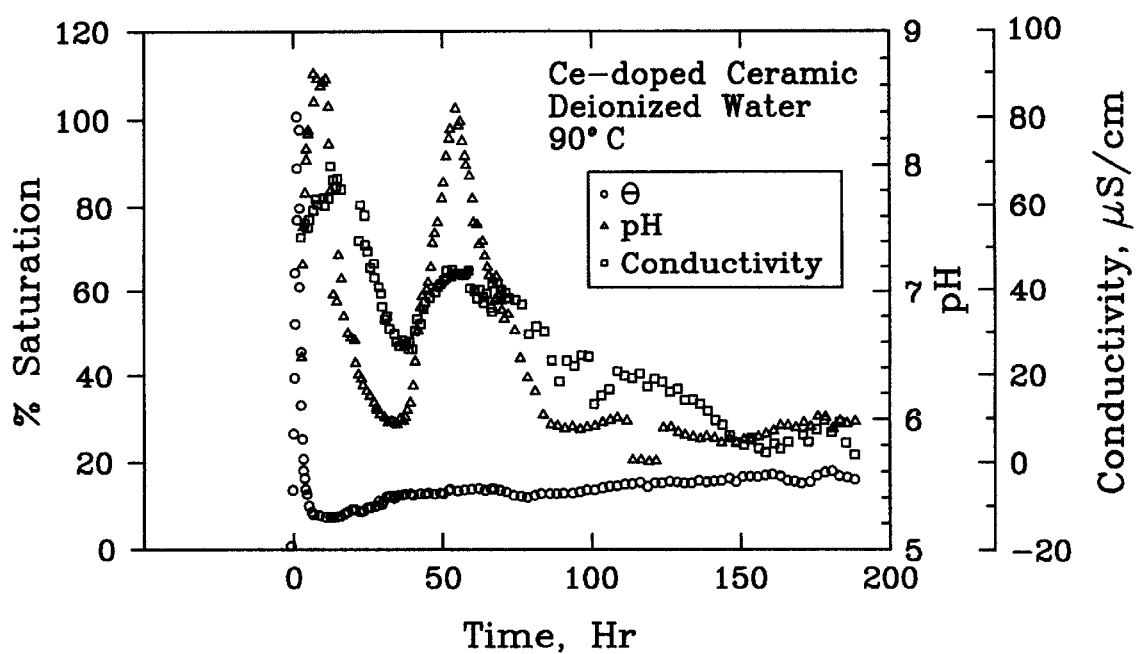
FIG. 7 is a graph of percent saturation, conductivity and pH versus time.
Figure 1:
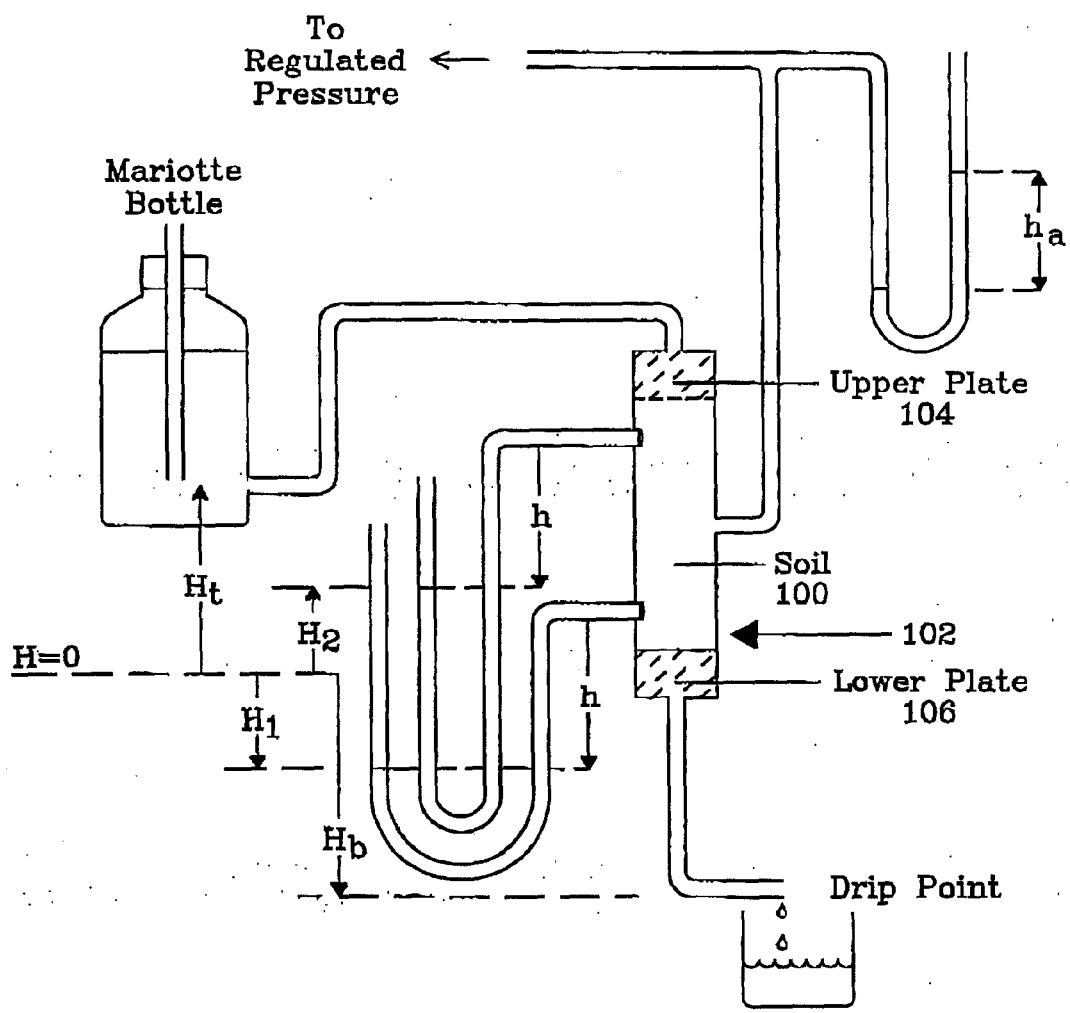

Results are shown in FIG. 7. The data show that several dissolution/precipitation events have occurred since approximately 930 hours into the test. However, there were some operational problems experienced during this run that may have affected the results. The flow rate was reduced to approximately 1 mL/d at about 1500 hr into the test to see if the variations in volumetric water content persisted at a lower rate of water influx. As shown in FIG. 7, after the flow rate reduction, the column has slowly drained over a period of several days to a steady, and very low water content (<5%).

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method for measuring coupled flow, transport and reaction processes in liquid unsaturated flow conditions in a porous material, the method comprising the steps of:
    (a) placing the porous material in a vessel, the vessel having porous plate below the porous material, the porous material having an amount of a liquid and an amount of a gas in an unsaturated condition;
    (b) maintaining the unsaturated condition by regulating a flow selected from the group consisting of a liquid flow, a gas flow, and a combination thereof, and collecting an effluent from an outlet; and
    (c) measuring parameters of a porous material bulk temperature, pressure, the liquid flow, vessel mass, the effluent chemistry, and combinations thereof as a function of time and at intervals of a maximum of 1 hour; wherein
    (d) analyzing said measured parameters provides the measuring of said coupled flow, transport and reaction processes within said porous material.

2. The method as recited in claim 1, wherein said maintaining includes heating the vessel to an elevated temperature.

3. The method as recited in claim 1, wherein said reaction processes include reaction with said gas.

4. The method as recited in claim 1, wherein said gas flow is through a pressure port into or from said vessel for periodically replenishing or venting said gas consumed in said reaction.

5. The method as recited in claim 1, wherein said measuring is with an automated data acquisition system permitting data collection of said parameters at least every 60 seconds.

6. An apparatus for measuring coupled flow, transport and reaction processes in liquid unsaturated flow conditions in a porous material, the apparatus comprising:
    (a) a vessel having a porous plate at a bottom end placed below the porous material, the porous material having an amount of a liquid and an amount of a gas in an unsaturated condition;
    (b) a liquid flow port through the top for maintaining the unsaturated condition by regulating a flow selected from the group consisting of a liquid flow, a gas flow, and a combination thereof, and an outlet for collecting effluent; and (c) instruments for measuring parameters of a porous material bulk temperature, a vessel pressure, the liquid flow, an effluent chemistry, and combinations thereof at intervals of a maximum of about 1 hour.

7. The apparatus as recited in claim 6, further comprising:

a pressure port near the top.

8. A method for measuring coupled flow, transport and reaction processes in liquid unsaturated flow conditions in a porous material, the method comprising the steps of:

(a) placing the porous material having an initial porosity in a vessel, the vessel having a porous plate below the porous material, the porous material having an amount of a liquid and an amount of a gas in an unsaturated condition;

(b) maintaining the unsaturated condition by regulating a flow selected from the group consisting of a liquid flow, a gas flow, and a combination thereof, and collecting an effluent from an outlet;

(c) changing the initial porosity to a second porosity;

(d) changing a pressure, corresponding to said changing of the initial porosity, of the flow selected from the group consisting of the liquid flow, the gas flow, and a combination thereof, for maintaining a liquid flow through the second porosity; and (e) measuring parameters of temperature, a vessel pressure, the liquid flow, the effluent chemistry, and combinations thereof during the maintaining, and changing.

9. The method as recited in claim 8, wherein said maintaining includes heating the vessel to an elevated temperature.

10. The method as recited in claim 8, wherein said changing of the initial porosity is by a reaction process.

11. The method as recited in claim 10, wherein said reaction process is a reaction of said porous material with said gas.

12. The method as recited in claim 11, wherein said gas flow is through a gas port into said vessel for periodically replenishing said gas consumed in said reaction.

13. The method as recited in claim 8, wherein said measuring is with an automated data acquisition system permitting data collection of said parameters at least every second.

* * * * *

UNITED STATES PATENT AND TRADEMARK OFFICE
CERTIFICATE OF CORRECTION

PATENT NO.    : 5,974,859
DATED         : November 2, 1999
INVENTOR(S)   : McGrail et al.

Figure 1:
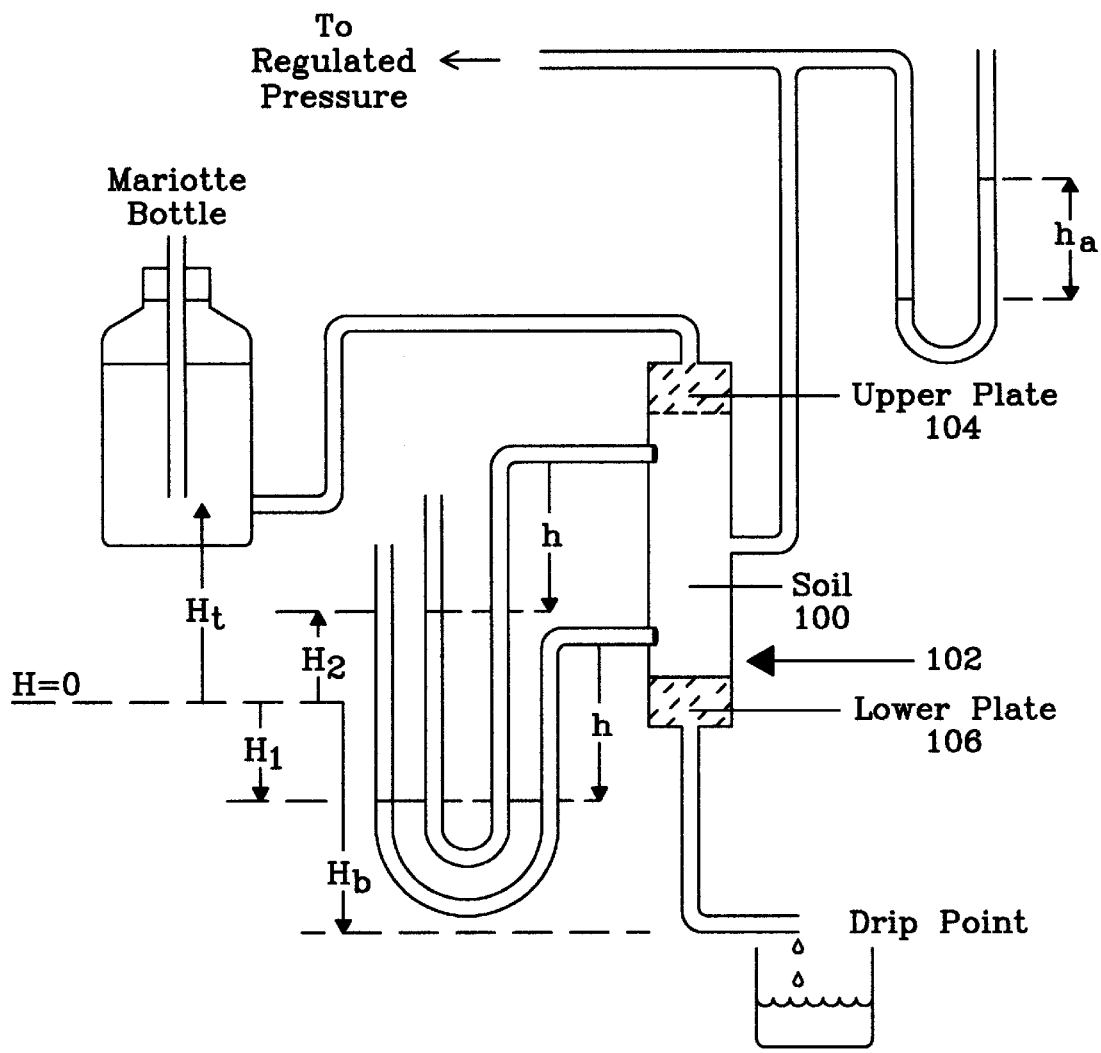
FIG. 1 is a cross section schematic of a prior art flow cell system for steady-state measurement of hydraulic conductivity of unsaturated soils.

It is certified that error appears in the above-identified patent and that said Letters Patent is hereby corrected as shown below:

Drawings,
Drawing sheet, consisting of Fig. 1, should be deleted to be replaced with the attached page.
Fig 4a Legend, unbold "Electrical Lines" and bold "Fluid lines, Normally Open"
Fig 4b unbold "Electrical Lines" and bold "Fluid lines, Normally Open"

Column 5,
Line 19, please replace "304" with -- 306 --.

Signed and Sealed this

Sixteenth Day of September, 2003

JAMES E. ROGAN
*Director of the United States Patent and Trademark Office*